(12) United States Patent
Patil

(10) Patent No.: US 8,663,623 B2
(45) Date of Patent: *Mar. 4, 2014

(54) HERBAL CATTLE FEED SUPPLEMENT COMPOSITIONS FOR ENHANCING PRODUCTIVITY AND QUALITY OF MILK

(76) Inventor: Prashant Neminath Patil, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 13/501,565

(22) PCT Filed: Oct. 12, 2009

(86) PCT No.: PCT/IN2009/000571
§ 371 (c)(1),
(2), (4) Date: Apr. 12, 2012

(87) PCT Pub. No.: WO2011/045801
PCT Pub. Date: Apr. 21, 2011

(65) Prior Publication Data
US 2012/0263697 A1    Oct. 18, 2012

(51) Int. Cl.
*A01N 63/00* (2006.01)

(52) U.S. Cl.
USPC ..................................... 424/93.51

(58) Field of Classification Search
None
See application file for complete search history.

(56) References Cited

U.S. PATENT DOCUMENTS

| 4,642,317 A | 2/1987 | Palmquist et al. ............ 514/558 |
| 6,080,401 A | 6/2000 | Reddy et al. ................. 424/93.3 |

FOREIGN PATENT DOCUMENTS

| DE | 202006000487 | 4/2006 |
| DE | 102006042149 | 5/2007 |
| KR | 20030044731 | 6/2003 |
| KR | 2009097727 | 9/2009 |
| WO | 0074696 | 12/2000 |
| WO | 2002003813 | 1/2002 |
| WO | WO 02/03813 | * 1/2002 | ............ A23K 1/165 |
| WO | 02026261 | 4/2002 |
| WO | 2004052122 | 6/2004 |
| WO | WO 2007/060539 A2 | * 5/2007 |

OTHER PUBLICATIONS

PCT Search Report for PCT/IN2009/000571, Jun. 18, 2010.
U.S. Appl. No. 13/501,574, filed Apr. 12, 2012, Patil.
U.S. Appl. No. 13/508,241, filed May 4, 2012, Patil.
U.S. Appl. No. 13/511,355, filed May 22, 2012, Patil.
Meeske, R. et al., The effect of concentrate supplementation on the productivity of grazing Jersey cows on a pasture based system. In: South African Journal of Animal Science, vol. 36/22006. pp. 105, 110, 2006.
Castillo, A.R. et al., Effects of feeding rations with genetically modified whole-cottonseed to lactating Holstein cows. In: Journal of Diary. Science, vol. 87/6, 2004. pp. 1778-1785.
PCT Search Report for PCT/IN10/000726, Apr. 24, 2011.
PCT Search Report for PCT/IN09/000572, Jun. 14, 2010.

* cited by examiner

*Primary Examiner* — Suzanne M Noakes
*Assistant Examiner* — Stephen Chong
(74) *Attorney, Agent, or Firm* — C. Rachal Winger; K&L Gates, LLP

(57) ABSTRACT

The present invention relates to multi purpose herbal cattle feed supplement compositions for enhancing the productivity and quality of milk by improved bioavailability/bioenhancing of nutrients. The herbal composition comprises an effective amount of an extract and/or at least one bioactive fraction or powder from herbs such as *Asparagus, Withania, Lepidium, Bacopa, Nardostachys, Vetiveria, Pueraria, Emblica, Tinospora* etc.; one or more additive selected from Probiotics, decorticated cotton seed extract (DCC), chelated mineral mixture, mineral nutrients, dicalcium phosphate (DCP), dolomite, calcite, vitamins and amino acids to obtain the herbal feed supplement compositions.

21 Claims, No Drawings

HERBAL CATTLE FEED SUPPLEMENT COMPOSITIONS FOR ENHANCING PRODUCTIVITY AND QUALITY OF MILK

CROSS REFERENCE TO RELATED APPLICATION

This application is a US national stage entry of PCT/IN09/00571 filed Oct. 12, 2009, which is incorporated by reference in its entirety herein.

FIELD OF THE INVENTION

The present invention relates to multi purpose herbal cattle feed supplement compositions for enhancing the productivity and quality of milk by improved bioavailability/bioenhancing of nutrients. The herbal composition comprises an effective amount of an extract and/or at least one bioactive fraction or powder from herbs such as *Asparagus, Withania, Lepidium, Bacopa, Nardostachys, Vetiveria, Pueraria, Emblica, Tinospora* etc.; one or more additive selected from Probiotics, decorticated cotton seed extract (DCC), chelated mineral mixture, mineral nutrients, dicalcium phosphate (DCP), dolomite, calcite, vitamins and amino acids to obtain the herbal feed supplement composition; and process for the preparation of such extracts and herbal cattle feed supplement compositions.

BACKGROUND OF THE INVENTION

Increasing the milk production of lactating dairy cattle along with the quality of the milk is an ongoing challenge facing the dairy industry. The challenge is complicated by the fact that, even though a dairy cattle diet can be provided with all the essential ingredients to meet her requirements, she may still face problem of bioavailability of the essential nutrients due to non-absorption of nutrients in the intestine at the levels required for higher milk production. One cause of this dilemma is the digestive system of the dairy cattle herself. Ingested feed first passes into the reticulo-rumen, where it is subject to anaerobic microbial fermentation. This microbial fermentation begins the digestive process and gives the ruminant the ability to utilize fibrous feeds that the mammalian system alone cannot break down due to the lack of necessary enzyme systems. The host cattle subsequently meets her own nutrient needs by utilizing the by-products of this extensive fermentation, along with any undigested feed residues and the resultant microbial mass that passes from the rumen. Ruminant species are able to effectively utilize dietary ingredients that are poorly used by monogastric species. This occurs because ruminants can ferment dietary ingredients in the reticulo-rumen compartment of their complex ruminant stomach.

Bioavailability of food is an important issue in nutrition. Bioavailability refers to the amount of a nutrient in a food that the body may ultimately use to perform specific physiological functions. Nutrients ingested but not released during the digestive process for absorption are of no nutritional value. "An assessment of the adequacy of dietary intakes of nutrients requires not only knowledge of the nutrient content of the foods ingested but also the extent to which the nutrient present in the diet is available for absorption and utilization [Sauberlich H E. Bioavailability of vitamins. Prog Food Nutr Sci. 1985; 9(1-2):1-33. Review. PMID: 3911266]. The term 'bioavailability' attempts to include in a single concept the effect of a sequence of metabolic events, i.e., digestibility, solubilization, absorption, organ uptake and release, enzymatic transformation, secretion and excretion [Bronner F. Nutrient bioavailability, with special reference to calcium. J Nutr. 1993 May; 123(5):797-802. Review. PMID: 8487089]. A number of factors affect bioavailability: factors contained in the food itself, factors of cattle physiology, factors specific to cattle health status, and factors related to the food processing.

Often, these above problems are addressed through the use of synthetic chemicals or hormones. U.S. Pat. No. 5,565,211 disclose a composition designed for improving the digestibility of feed for ruminants that contains an aromatic phenol derivative, an absorbing support, and an aromatizing mixture. U.S. Pat. No. 5,496,571 discloses a method for increasing the production of milk in ruminants that includes oral administration of an increasing amount of encapsulated choline. U.S. Pat. No. 4,704,276 discloses a method for increasing lactation in lactating ruminants that includes the administration of antibiotics. U.S. Pat. No. 4,857,332 discloses a composition for increasing milk fat production in ruminants that includes sodium and magnesium antacids, an electrolyte, and sodium bicarbonate. The WO 03068158 discloses the composition for increasing milk production in an cattle that includes an active compound chosen from calcium isopropyl cresol, calcium isopropyl-o-cresol, lactic acid, or combinations thereof, and calcium carbonate as a buffering agent.

There are few reports, which deal with the compositions containing natural agents such as herbs and probiotics. U.S. Pat. No. 6,060,050 discloses the probiotic composition which is particularly useful for inclusion in food products to enhance their nutritional value, comprises one or more probiotic microorganisms such as *Bifidobacterium* and a carrier to transport the microorganisms to the large bowel or other regions of the gastrointestinal tract. The invention disclosed in WO03043440 relates to a composition comprising a fungus and at least one growth-promoting component selected from the group comprising organic acids, inorganic acids, cattle feed antibiotics, conventional growth promoters, and plant extracts, prebiotics, probiotics, synbiotics, enzymes and herbs. U.S. Pat. No. 7,070,814 discloses bioavailability-facilitating composition comprising *Cuminum cyminum* along with herbal drugs and neutraceuticals. It highlights the increase in drug uptake in presence of *Cuminum cyminum*. US 20070009577 highlights the importance of Probiotic compositions in promoting the health of humans and other cattles. U.S. Pat. No. 5,145,695 discloses composition and method thereof for increasing milk production in diary cattle by balancing the essential amino acids via a particular complete feed, concentrate, or blender or base mix form of the composition which delivers essential amino acids post-ruminally.

So there are none of the compositions, which contain naturally occurring agents and which address both the problems of increasing the milk production along with improved quality by increase in Fat and SNF content. Hence the present inventor aim is to address the above problems without undesired side effects by developing a multi purpose herbal cattle feed supplement composition, mainly comprising:
 a) medicinal herbs,
 b) probiotics,
 c) DCC,
 d) chelated mineral mixture or mineral nutrients and
 e) DCP or dolomite or calcite.

The herbal revolution and its implementation to daily nutrient intake or function food/dietary supplements with desired therapeutic efficacy led the world populations great interest in the herbal compositions. This ultimately led to researchers to develop them in functional food and nutraceuticals and finally to develop marketable products. Functional foods are substances that provide health benefits beyond the normal nutritional values and nutrients added, which are not naturally occurring in that food is called as functional fortified food. The plants are the major source among the Indian masses, since most important foods of mankind as these are not only nutritive but are also sometimes indispensable for the maintenance of health. There are some herbal food supplements available in the developed nations and a few in the developing ones.

Probiotics are microorganisms that are beneficial to the health of an individual. There are a variety of probiotic microorganisms, which are suitable for use in feed supplement compositions including yeasts such as *Saccharomyces*, and bacteria such as the genera *Bifidobacterium, Bacteroides, Clostridium, Fusobacterium, Propionibacterium, Streptococcus, Enteroccus, Lactococcus, Staphylococcus, Peptostrentococcus* and *Lactobacillus*. Probiotics are predominately lactic acid producing bacteria. In contrast to herbal medicine, probiotics developed as a science only recently; and this science remains unacknowledged by many medical practitioners. Probiotics are widely present in nature and serve many beneficial functions. Biologically, they are classified as plants. They are non-pathogenic, do not produce toxins, and are considered natural and organic. They are essentially an opposite of antibiotics, which are inhibitory to other bacteria, including probiotic bacteria. These beneficial bacteria have an antagonistic effect on pathogenic bacteria, while antibiotics have an antagonistic effect on probiotics.

It would be desirable to more widely employ natural agents such as herbal mixtures and probiotics in order to benefit from their safe and beneficial activity. In particular, it would be desirable to use natural agents to induce a more rapid response from herbal medicines by stimulating their beneficial action. The desirability of a combination of natural agents would be dependent, however, upon the continued absence of adverse side effects.

To achieve the foregoing and other objects and in accordance with the purpose of the present invention, as embodied and broadly described herein, the compositions and process of preparation thereof.

OBJECTS OF THE INVENTION

It is a primary object of the present invention to provide novel herbal cattle feed supplement compositions for enhancing the productivity of milk in lactating dairy cattle, which is nontoxic and free from any side effects.

A further object of the invention is to provide herbal compositions as aforesaid which improves the quality of the milk by increasing the fat and SNF content.

A further object of the invention is to provide herbal compositions as aforesaid, which do not produce any undesirable byproducts, which can carry over into the cattle milk.

A further object of the invention is to provide herbal compositions as aforesaid, which are safe and practical to use with little technical expertise.

It is a further object of the present invention to provide herbal compositions having a long shelf life.

A further object of the invention is to provide herbal compositions as aforesaid, which are inexpensive and cost effective as compared to the existing compositions.

SUMMARY OF THE INVENTION

The invention relates generally to a multi purpose compositions of herbal cattle feed supplement for enhancing the productivity and quality of milk through improved bioavailability/bioenhancing of nutrients, which comprises an effective amount of an extract and/or at least one bioactive fraction or powder from herbs such as *Asparagus, Withania, Lepidium, Bacopa, Nardostachys, Vetiveria, Pueraria, Emblica, Tinospora* etc.; one or more additive selected from Probiotics, DCC, chelated mineral mixture, mineral nutrients, DCP, dolomite, calcite, vitamins and amino acids to obtain the herbal feed supplement composition; and process for the preparation of such extracts and herbal cattle feed supplement compositions.

By feeding the cattle multi purpose herbal cattle feed supplement composition along with the concentrate feed, the composition enhances the bioavailability of the diet nutrients in the intestine and which in turn increases the milk production along with the increase in fat and SNF content of the cattle milk.

STATEMENT OF THE INVENTION

Herbal cattle feed supplement compositions comprising effective amount of an extract and/or at least one bioactive fraction or powder from medicinal herbs and one or more additives selected from Probiotics, DCC, chelated mineral mixture, mineral nutrients, DCP, dolomite, calcite, vitamins and amino acids to obtain the herbal feed supplement composition. The medicinal herbs are selected from the group of *Asparagus, Withania, Lepidium, Bacopa, Nardostachys, Vetiveria, Pueraria, Emblica* and *Tinospora*. The medicinal herbs are essentially *Asparagus racemosus, Withania somnifera, Lepidium sativum, Bacopa monnieri, Nardostachys jatamamsi, Vetiveria zizanioides, Pueraria tuberosa, Emblica officinalis* and *Tinospora cordifolia*. The effective amount of an extract or bioactive fraction or powder ranges 15% to 40% (w/w) *Asparagus racemosus*, 10% to 30% (w/w) *Withania somnifera*, 05% to 25% (w/w) *Lepidium sativum*, 05% to 25% (w/w) *Bacopa monnieri*, 2.5% to 15% (w/w) *Nardostachys jatamamsi*, 05% to 25% (w/w) *Vetiveria zizanioides*, 5% to 25% (w/w) *Pueraria tuberosa*, 2.5% to 20% (w/w) *Emblica officinalis* and 2.5% to 20% (w/w) *Tinospora cordifolia*. The effective amount of an extract or bioactive fraction or powder more preferably 20% (w/w) *Asparagus racemosus*, 15% (w/w) *Withania somnifera*, 10% (w/w) *Lepidium sativum*, 10% (w/w) *Bacopa monnieri*, 5% (w/w) *Nardostachys jatamamsi*, 10% (w/w) *Vetiveria zizanioides*, 10% (w/w) *Pueraria tuberosa*, 10% (w/w) *Emblica officinalis* and 10% (w/w) *Tinospora cordifolia* of herbal mixture. The effective amount preferably comprises of 30 to 70% (w/w) herbal mixture, 5 to 10% (w/w) probiotics, 5 to 20% (w/w) DCC, 5 to 20% chelated mineral mixture or mineral mixture, 5 to 40% (w/w) DCP or dolomite or calcite. The effective amount more preferably comprises of 50% (w/w) herbal mixture, 10% (w/w) probiotics, 15% (w/w) DCC, 10% (w/w) chelated mineral mixture or mineral mixture, 15% (w/w) DCP or dolomite or calcite. The probiotics contains at least one stain of live yeast, preferably of *Saccharomyces cerevisiae* 47 in the range of 5 to 10% (w/w) of total composition preferably of *Saccharomyces cerevisiae* 47 in the proportion of 10% (w/w) of total composition. The protein source is selected from decorticated cotton seed extract or soya, preferably DCC in the effective amount of 10% (w/w) of total composition. The effective amount of menthomins chelated mineral mixture or mineral mixture is 10 to 20% (w/w) of total composition and preferably 10% (w/w) of total composition. The menthomins chelated minerals are including zinc, manganese, copper, cobalt, selenium, chromium and iodine. The effective amount of DCP or dolomite or calcite is 5 to 40% (w/w) of total composition and preferably 15% (w/w) of total composition. The vitamins mixture or amino acids mixture is added to the composition in the range of 0 to 1% (w/w) of total composition.

DETAILED DESCRIPTION OF THE INVENTION

The invention is for preparation of multi purpose compositions of herbal cattle feed supplement for enhancing the productivity and quality of milk through improved bioavailability/bioenhancing of nutrients, which comprises an effective amount of an extract and/or at least one bioactive fraction or powder from herbs and one or more additive selected from Probiotics, DCC, chelated mineral mixture, mineral nutrients, DCP, dolomite, calcite, vitamins and amino acids to obtain the herbal feed supplement composition.

The multi purpose compositions of herbal cattle feed supplement mainly comprises the following ingredients in the proportion as mentioned below:
1. Herbal Mixture—30 to 70% (w/w) of total composition;
2. Probiotics—5 to 10% (w/w) of total composition;
3. DCC—5 to 20% (w/w) of total composition;
4. Chelated Mineral Mixture or Mineral Mixture—5 to 20% (w/w) of total composition;
5. DCP or dolomite or calcite—5 to 40% (w/w) of total composition.
6. Vitamins—0 to 1% (w/w) of total composition and
7. Amino acids—0 to 1% (w/w) of total composition.

1. Herbal Mixture: The medicinal herbs which comprise the core of the cattle feed supplement compositions are selected from the following group:
*Asparagus racemosus*: Family—Liliaceae
*Withania somnifera*: Family—Solanaceae
*Lepidium sativum*: Family—Brassicaceae
*Bacopa monnieri*: Family—Scrophulariaceae
*Nardostachys jatamamsi*: Family—Valerianaceae
*Vetiveria zizanioides*: Family—Poaceae
*Pueraria tuberose*: Family—Fabaceae
*Emblica officinalis*: Family—Euphorbiaceae
*Tinospora cordifolia*: Family—Meninspermaceae

TABLE 1

Details of the medicinal herbs used in herbal cattle feed supplement compositions are as below:

| S. No | Latin Binomial | Common Names | Geographical Distribution | Parts Used | Quantity | Adverse Effects |
|---|---|---|---|---|---|---|
| 1 | *Asparagus racemosus* | Shatawari | Throughout India | Roots & Leaves | 15-40% Preferably 20% | None |
| 2 | *Withania somnifera* | Ashwagandha | Throughout India | Roots & Leaves | 10-30% Preferably 15% | None |
| 3 | *Lepidium sativum* | Haliv | Throughout India | Seeds | 5-25% Preferably 10% | None |
| 4 | *Bacopa monnieri* | Neerabrahmi | Throughout India | Entire Plant | 2.5-15% Preferably 10% | None |
| 5 | *Nardostachys jatamamsi* | Jatamamsi | Himalayan region | Roots | 15-40% Preferably 5% | None |
| 6 | *Vetiveria zizanioides* | Vekenth | Throughout India | Rhizomes | 5-25% Preferably 10% | None |
| 7 | *Pueraria tuberosa* | Bhuikovla | Throughout India | Roots | 5-25% Preferably 10% | None |
| 8 | *Emblica officinalis* | Amla | Throughout India | Fruits | 2.5-20% Preferably 10% | None |
| 9 | *Tinospora cordifolia* | Gudchi | Throughout India | Stem | 2.5-20% Preferably 10% | None |

2. Probiotics: The probiotics which is used in the composition essentially constitutes the live yeast culture in the range of 5 to 10% (w/w) of total composition preferably of *Saccharomyces cerevisiae* 47 in the proportion of 10% (w/w) of total composition.

3. Protein Source: The protein source is selected from decorticated cotton seed extract or soya; preferably decorticated cotton seed extract in the effective amount of 5 to 20% (w/w) of total composition and in preferred embodiment it is 10% (w/w) of total composition.

4. Chelated Minerals: The chelated minerals which mainly consists of the following:

| Chelated Mineral | % by weight |
| --- | --- |
| Zinc | 5 to 10 |
| Manganese | 1 to 4 |
| Copper | 0.5 to 2 |
| Cobalt | 0.05 to 0.25 |
| Selenium | 0.01 to 0.1 |
| Chromium | 0.05 to 0.2 |
| Iodine | 0.01 to 0.1 |
| Methomin | 5 to 60 |
| Tricalcium phosphate | 30 to 35 |

Preparation of Chelated Mineral Mixture: The chelated minerals preferably menthomins chelated are prepared by mixing 8% (w/w) zinc, 2% (w/w) manganese, 1.2% (w/w) copper, 0.12% (w/w) cobalt, 0.05% (w/w) selenium, 0.09% (w/w) chromium, 0.04% (w/w) iodine, methomin and tricalcium phosphate. The chelated mineral mixture is added to the herbal composition in a proportion of 5 to 20% (w/w) of total composition and preferable 10% (w/w) of total composition.

5. Mineral Mixture (MM): Mineral mixture contains of the following minerals in the designated proportions:

|  | BIS* Specs | MM of Invention |
| --- | --- | --- |
| Calcium Min. | 20.0% | 18-21% |
| Phosphorus Min. | 12.0% | 11-13% |
| Magnesium Min. | 5.0% | 4.5-5.5% |
| Copper Min | 0.10% | 0.08-0.12% |
| Zinc Min. | 0.80% | 0.7-0.9% |
| Manganese Min. | 0.12% | 0.10-0.14% |
| Iron Min. | 0.40% | 0.35-0.45% |
| Cobalt Min. | 0.012% | 0.010-0.014% |
| Iodine Min. | 0.026% | 0.024-0.028% |
| Sulphur | 1.8-3.0% | 1.8-3.0% |
| Total Ash | 78-85% | 78-85% |
| Moisture (Max.) | 5.0% | 4.0-5.5% |
| Fluorine (Max.) | 0.07% | 0.05-0.08% |
| Lead (Max.) | 7.0 ppm | 6-8 ppm |
| Arsenic (Max.) | 20.0 ppm | 18-22 ppm |
| Acid insoluble Ash (Max.) | 3.0% | 2.5-3.5% |

*BIS—Bureau of Indian Standard

The mineral mixture is added instead of chelated mineral mixture to the herbal composition in a proportion of 5 to 20% (w/w) of total composition and preferable 10% (w/w) of total composition.

6. Vitamins:

Mixture #1: The vitamins are mixed in the following proportion—

| Vitamin | Nutritional value per gram |
| --- | --- |
| Vitamin A | 80,000-85,000 IU |
| Vitamin $D_3$ | 10,000-15,000 IU |
| Vitamin K | 8-12 mg |
| Vitamin $B_2$ | 40-60 mg |
| Vitamin $B_{12}$ | 12-18 mcg |

Mixture #2: The vitamins are mixed in the following proportion—

| Vitamin | Nutritional value per gram |
| --- | --- |
| Vitamin $B_1$ | 7-9 mg |
| Vitamin $B_2$ | 3-5 mg |
| Vitamin $B_6$ | 14-18 mg |
| Vitamin $B_{12}$ | 70-90 mcg |
| Niacin | 110-130 mg |
| Folic Acid | 3.0-4.0 mg |
| Vitamin E | 75-85 mg |

The vitamin mixture #1 or #2 may be added to the herbal composition in a proportion of 0 to 1% (w/w) of total composition.

7. Amino acids: Essential amino acids mixture is prepared. The amino acids mixture may be added to the herbal composition in a proportion of 0 to 1% (w/w) of total composition.

The composition of an effective amount of an extract and/or at least one bioactive fraction or powder from medicinal herbs such as *Asparagus racemosus, Withania somnifera, Lepidium sativum, Bacopa monnieri, Nardostachys jatamamsi, Vetiveria zizanioides, Pueraria tuberosa, Emblica officinalis, Tinospora cordifolia* etc.; one or more additive selected from Probiotics, DCC, chelated mineral mixture, mineral nutrients, DCP, vitamins and amino acids to obtain the herbal feed supplement composition; balanced to deliver necessary functions at a particular point in the cattle's digestive system. By properly adjusting a particular component in the feed supplement composition to make bioavailability of essential nutrients in the intestine of cattle for absorption, which enhances the overall production of milk and also the quality of milk.

The synergistic formulation also acts as a preventive measure for dairy cattle by boosting the natural defense mechanism, strengthening the anti-oxidant mechanism and also by maintaining healthy epithelial and keratin lining.

Apart from the herbs and probiotic the feed supplement composition also includes protein source such as DCC, chelated minerals, mineral mixture and DCP. DCP serves as source of calcium and phosphate and along with the chelated minerals or mineral mixture balance the cattle diet.

The synergistic action of the medicinal herbs and enzymes of the probiotic such as yeast enhances the digestibility of the food and in turn enhances the bioavailability of the nutrients in the intestine of cattle for absorption which ultimately increases the milk productivity and quality.

The compositions can be used in several forms: powdered feed form, concentrate form, blender form and base mix form.

Process for Preparation of Herbal Cattle Feed Supplement

Method-I

The present invention herbal feed supplement compositions are prepared by one type of method comprising the following steps:
a) Obtaining the part of medicinal herb from a group comprising leaves, bark, root and aerial parts;
b) drying the plant part of step (a);
c) powdering the dried plant material of step (b) to a coarse powder;
d) the dried and powdered plant material obtained in step (c) can be used directly to prepare the feed compositions by mixing the effective amount by weight of medicinal herb selected from the group of *Asparagus racemosus, Withania somnifera, Lepidium sativum, Bacopa monnieri, Nardostachys jatamamsi, Vetiveria zizanioides, Pueraria tuberose, Emblica officinalis* and *Tinospora cordifolia* to obtain the herbal composition;
e) the above herbal composition is added with at least one of the ingredient selected from Probiotics, DCC, chelated mineral mixture, mineral nutrients, DCP, dolomite, calcite, vitamins and amino acids to obtain the herbal feed supplement composition.

Method-II

The present invention herbal feed supplement compositions are prepared by another type of method comprising the steps as below:
a) Obtaining the part of medicinal herb from a group comprising leaves, bark, root and aerial parts;
b) drying the plant part of step (a);
c) powdering the dried plant material of step (b) to a coarse powder;
d) extracting the powdered dried plant material at a temperature in the range of 30 to 85° C.;
e) extracting the plant material with water or alcohol or mixture of both for a period ranges from 6 hours to 6 days;
f) concentrating the obtained extract under reduced pressure at a temperature in the range of 40 to 85° C.;
g) the concentrated extract is subjected to removal of solvent;
h) mixing the effective amount by weight of above concentrated extract of medicinal herb selected from the group of *Asparagus racemosus, Withania somnifera, Lepidium sativum, Bacopa monnieri, Nardostachys jatamamsi, Vetiveria zizanioides, Pueraria tuberosa, Emblica officinalis* and *Tinospora cordifolia* to obtain the herbal composition;
i) the above herbal composition is added with one or more of the ingredient selected from Probiotics, DCC, chelated mineral mixture, mineral nutrients, DCP, dolomite, calcite, vitamins and amino acids to obtain the herbal feed supplement composition.

EXAMPLES

The following specific examples presented to illustrate the herbal cattle feed supplement compositions are prepared by above said method I but do not limit the scope of the invention and additional compositions are being prepared and tested.

TABLE 2

Specific herbal mixtures prepared are as following:

A)

| Medicinal Herb | Composition (% by weight) | | | | | | | | |
|---|---|---|---|---|---|---|---|---|---|
| | I | II | III | IV | IV | VI | VII | VIII | IX |
| *Asparagus racemosus* | 20 | 22.5 | 25 | 20 | 21.66 | 23.33 | 18.75 | 20 | 22.5 |
| *Withania somnifera* | 17.5 | 17.5 | 20 | 13.33 | 15 | 16.66 | 16.25 | 17.5 | 18.75 |
| *Lepidium sativum* | 12.5 | 10 | 7.5 | 11.66 | 10 | 8.33 | 10 | 11.25 | 11.25 |
| *Bacopa monnieri* | 12.5 | 10 | 7.5 | 11.66 | 13.33 | 11.66 | 10 | 8.75 | 7.5 |
| *Nardostachys jatamamsi,* | 7.5 | 05 | 10 | 6.66 | 10 | 8.33 | 05 | 6.25 | 7.5 |
| *Vetiveria zizanioides* | 10 | 12.5 | 7.5 | 11.66 | 8.33 | 10 | 10 | 8.75 | 7.5 |
| *Pueraria tuberosa* | 10 | 12.5 | 12.5 | 11.66 | 8.33 | 6.66 | 10 | 10 | 8.75 |
| *Emblica officinalis* | 05 | 05 | 05 | 11.66 | 05 | 6.66 | 10 | 8.75 | 7.5 |
| *Tinospora cordifolia* | 05 | 05 | 05 | 11.66 | 8.33 | 8.33 | 10 | 8.75 | 7.5 |

B)

| Ingredient | Composition (% by weight) | | | | | | | | | | | | | | | | | |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 |
| Herbal Mixture | 35 | 40 | 45 | 50 | 60 | 65 | 40 | 35 | 40 | 50 | 60 | 60 | 60 | 60 | 60 | 50 | 45 | 40 |
| Live yeast Culture | 2.5 | 05 | 7.5 | 10 | 05 | 2.5 | 2.5 | 05 | 7.5 | 10 | 12.5 | 15 | 12.5 | 10 | 7.5 | 10 | 12.5 | 15 |
| DCC | 7.5 | 10 | 12.5 | 10 | 10 | 7.5 | 7.5 | 10 | 12.5 | 10 | 7.5 | 05 | 2.5 | 05 | 7.5 | 10 | 12.5 | 15 |
| Chelated Mineral Mixture | 20 | 20 | 15 | 15 | 10 | 10 | 20 | 15 | 15 | 15 | 10 | 10 | 10 | 10 | 10 | 15 | 15 | 10 |
| DCP | 35 | 25 | 20 | 15 | 15 | 15 | 30 | 35 | 25 | 15 | 10 | 10 | 15 | 15 | 15 | 15 | 15 | 20 |

TABLE 2-continued

Specific herbal mixtures prepared are as following:

| Ingredient | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| Vitamins | — | — | — | — | — | — | — | — | — | — | — | — | — | — | — | — | — | — |
| Amino acids | — | — | — | — | — | — | — | — | — | — | — | — | — | — | — | — | — | — |

C)

Composition (% by weight)

| Ingredient | 19 | 20 | 21 | 22 | 23 | 24 | 25 | 26 | 27 | 28 | 29 | 30 | 31 | 32 | 33 | 34 | 35 | 36 |
|---|---|---|---|---|---|---|---|---|---|---|---|---|---|---|---|---|---|---|
| Herbal Mixture | 65 | 60 | 50 | 45 | 35 | 35 | 60 | 50 | 45 | 40 | 40 | 35 | 50 | 50 | 50 | 50 | 50 | 50 |
| Live yeast Culture | 05 | 10 | 10 | 10 | 15 | 10 | 10 | 10 | 10 | 10 | 10 | 10 | 10 | 10 | 10 | 15 | 15 | 15 |
| DCC | 10 | 12.5 | 10 | 7.5 | 05 | 7.5 | 10 | 10 | 10 | 10 | 10 | 10 | 10 | 10 | 10 | 10 | 10 | 10 |
| Chelated Mineral Mixture | 10 | 10 | 15 | 17.5 | 20 | 22.5 | 10 | 15 | 15 | 15 | 10 | 10 | 15 | 15 | 15 | 10 | 10 | 10 |
| DCP | 10 | 10 | 15 | 20 | 25 | 25 | 10 | 15 | 20 | 25 | 30 | 35 | 14.5 | 14.5 | 14.2 | 14 | 13.5 | 13.5 |
| Vitamins | — | — | — | — | — | — | — | — | — | — | — | — | 0.2 | 0.4 | 0.6 | 0.8 | 1 | 0.5 |
| Amino acids | — | — | — | — | — | — | — | — | — | — | — | — | 0.3 | 0.1 | 0.2 | 0.2 | 0.5 | 1 |

Herbal cattle feed supplement compositions having a unique blend of herbal extracts of medicinal plants probiotic, DCC, chelated mineral mixture, mineral nutrients, DCP, dolomite, calcite, vitamins and amino acids etc. Herbal extracts of medicinal plants act as a galactagogue, immuno-booster and anti-depressant. Probiotic improves bioavailability of feed intake, increases lactation length and prevents acidosis. DCC acts as protein source. Chelated minerals and mineral mixtures balance the diet by providing various mineral mixture supplementations and nourish the cattle.

Field Trials on Buffaloes

METHODOLOGY: Total 12 lactating Murrah Buffaloes were selected for the study with the history of normal parturition. The selected Buffaloes were equally divided into two groups by consideration lactation days. Group I- and Group-II are pertaining to Treatment and Control Groups respectively. Each group contains 6 Buffaloes. The average lactation days of selected Buffaloes were between 65 to 130 days. All selected Buffaloes were maintained under usual farm management practices. Each Buffalo in Group I was fed 30 g/day of herbal composition individually with concentrate mixture for 60 days period. The Buffaloes in Group II were receiving concentrate mixture as per the routine farm management practice. The milk yield of each Buffalo was recorded twice in a week and milk samples from each Buffalo were collected at weekly interval for analysis of Fat, SNF and total Protein.

Results

The results are summarized in Tables 3 and 4 for Treatment and Control Groups of Buffaloes respectively.

TABLE 3

Treatment group

| Animal Number | Lactation days | Total milk yield of 60 days | Avg. milk yield/day (L) | Avg. Fat (%) | Avg. Fat yield (Kg) | Avg. SNF (%) | Avg. Protein (%) | Avg. protein yield (Kg) | Avg. Total solids Yield (Kg) |
|---|---|---|---|---|---|---|---|---|---|
| A | 89 | 489.25 | 7.77 | 9.07 | 0.70 | 10.53 | 4.61 | 0.36 | 1.59 |
| B | 65 | 503.15 | 7.99 | 9.92 | 0.79 | 11.33 | 4.50 | 0.36 | 1.70 |
| C | 130 | 489.40 | 7.77 | 8.88 | 0.69 | 10.76 | 4.53 | 0.37 | 1.51 |
| D | 98 | 495.00 | 7.86 | 8.94 | 0.70 | 11.58 | 4.62 | 0.38 | 1.61 |
| E | 106 | 648.15 | 10.29 | 8.94 | 0.91 | 10.88 | 4.54 | 0.49 | 2.02 |
| F | 105 | 542.50 | 8.61 | 9.74 | 0.84 | 11.14 | 4.62 | 0.41 | 1.81 |
| Average | — | 527.91 | 8.38 | 9.25 | 0.77 | 11.04 | 4.57 | 0.38 | 1.70 |

TABLE 4

Control group

| Animal Number | Lactation days | Total milk yield of 60 days | Avg. milk yield/day (L) | Avg. Fat (%) | Avg. Fat yield (Kg) | Avg. SNF (%) | Avg. Protein (%) | Avg. protein yield (Kg) | Avg. Total solids Yield (Kg) |
|---|---|---|---|---|---|---|---|---|---|
| 1 | 100 | 319.75 | 5.08 | 8.83 | 0.45 | 11.18 | 4.44 | 0.23 | 1.02 |
| 2 | 93 | 334.65 | 5.31 | 8.21 | 0.44 | 11.17 | 4.37 | 0.23 | 1.03 |
| 3 | 96 | 370.51 | 5.88 | 8.84 | 0.52 | 10.86 | 4.28 | 0.25 | 1.16 |
| 4 | 127 | 553.9 | 8.79 | 8.27 | 0.73 | 11.35 | 4.57 | 0.40 | 1.73 |
| 5 | 120 | 515.51 | 8.18 | 9.22 | 0.75 | 10.97 | 4.34 | 0.35 | 1.65 |
| 6 | 75 | 433.75 | 6.88 | 9.30 | 0.64 | 10.30 | 4.21 | 0.29 | 1.34 |
| Average | — | 421.35 | 6.69 | 8.78 | 0.59 | 10.97 | 4.37 | 0.29 | 1.32 |

Mild Yield

From Table 3 and 4 it is clear that the average milk yield after sixty days period for Treatment and Control Groups were 527.91 L and 421.35 L, respectively. The average milk yield of Treatment and Control Groups were 8.38 L and 6.69 L/day, respectively. From the statistical analysis, there is significant rise (1.7 L/day) in milk yield of Treatment Group as compared to Control (P<0.05; Table 5)

TABLE 5 t-Test: Paired Two Sample for Means

| | Variable 1 | Variable 2 |
|---|---|---|
| Mean | 8.379497 | 6.688016 |
| Variance | 0.974768 | 2.369036 |
| Observations | 6 | 6 |
| Pearson Correlation | 0.503131 | |
| Hypothesized Mean Difference | 0 | |
| Df | 5 | |
| t Stat | 3.075705 | |
| P(T <= t) one-tail | 0.013802 | |
| t Critical one-tail | 2.015048 | |
| P(T <= t) two-tail | 0.027604 | |
| t Critical two-tail | 2.570582 | |

Fat Yield

From Table 3 and 4 it is clear that the average fat for the sixty days period for Treatment and Control Groups were 9.25 and 8.78%, respectively. The average fat yield after sixty days period for Treatment and Control Groups were 0.77 and 0.59 kg/day, respectively. From the statistical analysis, there was significant rise (0.2 kg/day) in fat yield of Treatment Group as compared to Control (P<0.05, Table 6)

TABLE 6 t-Test: Paired Two Sample for Means

| | Variable 1 | Variable 2 |
|---|---|---|
| Mean | 0.771643508 | 0.588362 |
| Variance | 0.008527488 | 0.019141 |
| Observations | 6 | 6 |
| Pearson Correlation | 0.448058229 | |
| Hypothesized Mean Difference | 0 | |
| Df | 5 | |
| t Stat | 3.525099557 | |
| P(T <= t) one-tail | 0.008413692 | |
| t Critical one-tail | 2.015048372 | |
| P(T <= t) two-tail | 0.016827385 | |
| t Critical two-tail | 2.570581835 | |

Protein Yield

From Table 3 and 4 it is evident that the average protein after sixty days period for Treatment and Control Groups were 4.57 and 4.37%, respectively. The average protein yield after sixty days period for Treatment and Control Groups were 0.38 kg and 0.29 kg/day, respectively. From the statistical analysis, there is significant rise (0.09 kg/day) in protein yield of Treatment Group as compared to Control (P<0.05, Table 7).

TABLE 7 t-Test: Paired Two Sample for Means

| | Variable 1 | Variable 2 |
|---|---|---|
| Mean | 0.382809975 | 0.292745 |
| Variance | 0.001909173 | 0.004931 |
| Observations | 6 | 6 |
| Pearson Correlation | 0.45584413 | |
| Hypothesized Mean Difference | 0 | |
| Df | 5 | |
| t Stat | 3.4695782 | |
| P(T <= t) one-tail | 0.008928725 | |
| t Critical one-tail | 2.015048372 | |
| P(T <= t) two-tail | 0.01785745 | |
| t Critical two-tail | 2.570581835 | |

Total Solid Yield

From Table 3 and 4 it is evident that the average total solid yield after sixty days period for Treatment and Control Groups were 1.70 and 1.32 kg/day, respectively. From the statistical analysis, there is significant rise (0.37 kg/day) in total solid yield of Treatment Group as compared to Control (P<0.05, Table 8).

TABLE 8 t-Test: Paired Two Sample for Means

| | Variable 1 | Variable 2 |
|---|---|---|
| Mean | 1.695601158 | 1.321457 |
| Variance | 0.038181541 | 0.094346 |
| Observations | 6 | 6 |
| Pearson Correlation | 0.513527637 | |
| Hypothesized Mean Difference | 0 | |
| Df | 5 | |
| t Stat | 3.442210062 | |
| P(T <= t) one-tail | 0.009195733 | |
| t Critical one-tail | 2.015048372 | |
| P(T <= t) two-tail | 0.018391466 | |
| t Critical two-tail | 2.570581835 | |

Conclusion

It is evident from the above results depicted in Table 3 and 4 along with their respective t-Tests, that all the productive parameters related to milk production (Milk yield, Fat yield, SNF, Protein yield and total Solids) were showed significant enhancement in Treatment Group as compared to Control Group. The feeding of herbal composition fetched additional milk of 1.7 L/day in the Treatment Group. Herbal composition has not only maintained the level of milk yield in summer but has also showed enhancement in milk yield even in seasonal variations (May and July).

Field Trials on Cows

The field trials were conducted on total 10 lactating H.F., Jersey—H.F. Cross, Gir-Jersey Cross Cows were selected for the trials with the history of normal parturition. The field trials were conducted twice to ascertain the efficacy of herbal composition. The average lactation days of selected cows varied from 49 to more than 300 days. All selected cows were maintained under usual farm management practices. Each cow was fed 30 g/day of herbal composition individually with concentrate mixture along with dry and green fodders. The milk yield, Fat and SNF of each cow were recorded daily.

Results

The summary results are given in Table 9 and 10 for Treatment and Control Groups of Cows respectively.

TABLE 9

Comparison of Milk yield, Fat yield and total Solids before and during feeding of herbal composition (First Trial Run)

| Animal ID | Lactation days | Avg. Milk yield (L) | | Avg. Fat (%) | | Avg. Fat yield (L) | | Avg. Total Solids (%) | | Avg. Total solids Yield (Kg) | |
|---|---|---|---|---|---|---|---|---|---|---|---|
| | | Before | During | Before | During | Before | During | Before | During | Before | During |
| 8601 | 120 | 26.0 | 29.2 | 3.7 | 4.19 | 0.97 | 1.22 | 12.0 | 13.08 | 3.13 | 3.82 |
| 8602 | 115 | 19.9 | 22.5 | 3.8 | 4.17 | 0.74 | 0.94 | 12.0 | 13.05 | 2.39 | 2.95 |
| 8603 | 240 | 20.0 | 20.8 | 3.9 | 4.19 | 0.74 | 0.87 | 12.2 | 13.15 | 2.41 | 2.73 |
| 8604 | 49 | 14.3 | 16.6 | 3.7 | 4.19 | 0.53 | 0.69 | 12.0 | 13.15 | 1.73 | 2.17 |
| 8605 | 695 | 8.2 | 8.3 | 3.6 | 4.14 | 0.30 | 0.35 | 12.1 | 13.05 | 0.99 | 1.09 |
| 8606 | 66 | 11.8 | 12.5 | 3.8 | 4.19 | 0.43 | 0.52 | 12.2 | 13.09 | 1.42 | 1.64 |
| 8607 | 86 | 13.0 | 15.7 | 3.7 | 4.18 | 0.48 | 0.66 | 12.0 | 13.11 | 1.56 | 2.05 |
| 8608 | 356 | 9.5 | 10.7 | 3.6 | 4.17 | 0.35 | 0.44 | 12.0 | 13.11 | 1.15 | 1.39 |
| 8609 | 150 | 11.5 | 11.7 | 3.8 | 4.19 | 0.42 | 0.49 | 12.0 | 13.08 | 1.38 | 1.53 |
| 5430 | 365 | 11.2 | 12.1 | 3.5 | 4.20 | 0.42 | 0.50 | 11.8 | 13.12 | 1.35 | 1.58 |
| Avg. | — | 14.5.4 | 16.01 | 3.7 | 4.18 | 0.54 | 0.67 | 12.03 | 13.10 | 1.75 | 2.10 |

TABLE 10

Comparison of Milk yield, Fat yield and total Solids before and repeat feeding of herbal composition (Second Trial Run)

| Animal ID | Lactation days | Avg. Milk yield (L) | | Avg. Fat (%) | | Avg. Fat yield (L) | | Avg. Total Solids (%) | | Avg. Total solids yield (Kg) | |
|---|---|---|---|---|---|---|---|---|---|---|---|
| | | Before | Repeat | Before | Repeat | Before | Repeat | Before | Repeat | Before | Repeat |
| 8601 | 120 | 24.5 | 25.8 | 3.7 | 4.3 | 0.91 | 1.08 | 12.3 | 13.1 | 2.99 | 3.35 |
| 8602 | 115 | 19.6 | 21.4 | 3.6 | 4.2 | 0.72 | 0.90 | 12.1 | 13.0 | 2.39 | 2.78 |
| 8603 | 240 | 20.4 | 20.6 | 3.7 | 4.1 | 0.76 | 0.87 | 12.5 | 12.9 | 2.50 | 2.68 |
| 8604 | 49 | 14.3 | 15.3 | 3.6 | 4.0 | 0.53 | 0.64 | 12.3 | 12.8 | 1.75 | 1.98 |
| 8605 | 695 | 8.3 | 8.3 | 3.6 | 4.2 | 0.31 | 0.33 | 12.1 | 13.0 | 1.01 | 1.04 |
| 8606 | 66 | 11.8 | 12.2 | 3.8 | 4.3 | 0.44 | 0.48 | 12.4 | 13.1 | 1.45 | 1.53 |
| 8607 | 86 | 12.8 | 13.9 | 3.8 | 4.2 | 0.47 | 0.58 | 12.2 | 13.0 | 1.56 | 1.81 |
| 8608 | 356 | 9.8 | 10.5 | 3.8 | 4.2 | 0.36 | 0.44 | 12.3 | 13.0 | 1.20 | 1.37 |
| 8609 | 150 | 10.5 | 10.9 | 3.8 | 4.3 | 0.39 | 0.46 | 12.1 | 13.1 | 1.28 | 1.42 |
| 5430 | 365 | 10.2 | 10.7 | 3.6 | 4.2 | 0.38 | 0.45 | 11.9 | 13.0 | 1.25 | 1.40 |
| Avg | — | 14.22 | 14.96 | 3.70 | 4.20 | 0.53 | 0.62 | 12.22 | 13.00 | 1.74 | 1.94 |

Milk Yield

TABLE 11 t-Test: Paired Two Sample for Means

| | Variable 1 | Variable 2 |
|---|---|---|
| First Trial Run | | |
| Mean | 16.01 | 14.54 |
| Variance | 41.47877778 | 31.756 |
| Observations | 10 | 10 |
| Pearson Correlation | 0.991479105 | |
| Hypothesized Mean Difference | 0 | |
| df | 9 | |
| t Stat | 4.130162286 | |
| P(T <= t) one-tail | 0.001279434 | |
| t Critical one-tail | 1.833112923 | |
| P(T <= t) two-tail | 0.002558869 | |
| t Critical two-tail | 2.262157158 | |
| Second Trial Run | | |
| Mean | 14.96 | 14.22 |
| Variance | 33.16933333 | 29.475111 |
| Observations | 10 | 10 |

TABLE 11-continued t-Test: Paired Two Sample for Means

| | Variable 1 | Variable 2 |
|---|---|---|
| Pearson Correlation | 0.996832359 | |
| Hypothesized Mean Difference | 0 | |
| df | 9 | |
| t Stat | 4.222639006 | |
| P(T <= t) one-tail | 0.001115367 | |
| t Critical one-tail | 1.833112923 | |
| P(T <= t) two-tail | 0.002230734 | |
| t Critical two-tail | 2.262157158 | |

In the first trial run, the average milk yield before and during feeding were 145.4 L and 160.00 L, respectively. From the statistical analysis, there is significant rise (1.47 L/day) in milk yield during feeding of herbal composition as compared to before feeding period. In the second trial run, the average mild yield before and repeat feeding were 142.2 L and 149.6 L, respectively. From the statistical analysis, there is significant rise (0.74 L/day) in milk yield during feeding of herbal composition as compared to before feeding.

Fat Yield

TABLE 12 t-Test: Paired Two Sample for Means

|  | Variable 1 | Variable 2 |
|---|---|---|
| First Trial Run | | |
| Mean | 0.667 | 0.538 |
| Variance | 0.072801111 | 0.04479556 |
| Observations | 10 | 10 |
| Pearson Correlation | 0.993152004 | |
| Hypothesized Mean Difference | 0 | |
| Df | 9 | |
| t Stat | 6.320526329 | |
| P(T <= t) one-tail | 6.87959E−05 | |
| t Critical one-tail | 1.833112923 | |
| P(T <= t) two-tail | 0.000137592 | |
| t Critical two-tail | 2.262157158 | |
| Second Trial Run | | |
| Mean | 0.623 | 0.527 |
| Variance | 0.060556667 | 0.04049 |
| Observations | 10 | 10 |
| Pearson Correlation | 0.993798864 | |
| Hypothesized Mean Difference | 0 | |
| df | 9 | |
| t Stat | 5.923368502 | |
| P(T <= t) one-tail | 0.00011127 | |
| t Critical one-tail | 1.833112923 | |
| P(T <= t) two-tail | 0.000222539 | |
| t Critical two-tail | 2.262157158 | |

In first trial run, the average fat yield before and during feeding are 0.54 and 0.67 kg/day, respectively. From the statistical analysis, that there is significant rise (0.13 kg./day) in Fat yield during feeding of herbal composition as compared to before feeding. In second trial run, the average fat yield before and during feeding are 0.53 and 0.62 kg/day, respectively. From the statistical analysis, there is significant rise (0.09 kg/day) in Fat yield during feeding of herbal composition as compared to before feeding.

Total Solids

TABLE 13 t-Test: Paired Two Sample for Means

|  | Variable 1 | Variable 2 |
|---|---|---|
| First Trial Run | | |
| Mean | 2.094 | 1.751 |
| Variance | 0.714048889 | 0.458832222 |
| Observations | 10 | 10 |
| Pearson Correlation | 0.991917525 | |
| Hypothesized Mean Difference | 0 | |
| Df | 9 | |
| t Stat | 5.611901781 | |
| P(T <= t) one-tail | 0.000164611 | |
| t Critical one-tail | 1.833112923 | |
| P(T <= t) two-tail | 0.000329222 | |
| t Critical two-tail | 2.262157158 | |
| Second Trial Run | | |
| Mean | 1.936 | 1.738 |
| Variance | 0.569404444 | 0.439484444 |
| Observations | 10 | 10 |

TABLE 13-continued t-Test: Paired Two Sample for Means

|  | Variable 1 | Variable 2 |
|---|---|---|
| Pearson Correlation | 0.995540174 | |
| Hypothesized Mean Difference | 0 | |
| df | 9 | |
| t Stat | 5.520865741 | |
| P(T <= t) one-tail | 0.000185035 | |
| t Critical one-tail | 1.833112923 | |
| P(T <= t) two-tail | 0.00037007 | |
| t Critical two-tail | 2.262157158 | |

In the first trial run, the average total solids yield before and after feeding were 1.80 and 1.20 kg/day, respectively. From the statistical analysis, there is significant rise (0.30 kg/day) in total Solids during feeding of herbal composition as compared to before feeding. In the second trial run, the average total solids yield before and after feeding are 1.73 and 1.94 kg/day, respectively. From the statistical analysis, there is significant rise (0.20 kg/day,) in total Solids during feeding of herbal composition as compared to before feeding.

It is evident from the above results depicted in Table 9 and 10 along with their respective t-Tests that all the parameters related to milk production (Milk yield, Fat yield, and total Solids) were showed significant increase during feeding of herbal composition as compared to before feeding. Herbal composition has not only maintained the level of milk yield in summer but has also showed enhancement in milk yield even in seasonal variations (March and July). The feeding of herbal composition fetched additional milk of 1 L/day (Average of First and Second trial run in cross breed cows). It is also evident that the effect of herbal composition is irrespective of lactation stage and the beneficial effects are consistent even in the lactation stage.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. It is anticipated that one or more members of a group can be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein can be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that can be employed are within the scope of the invention. Thus, by way of example, but not of limitation, alternative configurations of the present invention can be utilized in accordance with the teachings herein. Accordingly, the present invention is not limited to that precisely as shown and described.

The invention claimed is:

1. A process for preparation of herbal cattle feed supplement compositions comprising:
   a. obtaining a part of medicinal herb from a group comprising leaves, bark, root and aerial parts;
   b. drying the plant part of step (a);
   c. powdering the dried plant material of step (b) to a coarse powder;
   d. mixing the effective amount by weight of the powdered or the concentrated extract of medicinal herb to obtain an herbal mixture; and,
   e. adding to the above herbal mixture one or more ingredients selected from Probiotics, DCC, chelated mineral mixture, mineral nutrients, DCP, dolomite, calcite, vitamins and amino acids to obtain the herbal feed supplement composition.

2. An herbal cattle feed supplement composition comprising (i) herbs *Asparagus racemosus, Withania somnifera, Lepidium sativum, Bacopa monnieri, Nardostachys jatamamsi, Vetiveria zizanioides, Pueraria tuberosa, Emblica officinalis* and *Tinospora cordifolia* or extracts, bioactive fractions or powders therefrom; and (ii) additives comprising (a) probiotics, (b) minerals, (c) protein source, (d) vitamins (e) amino acids and (f) dicalcium phosphate, dolomite or calcite.

3. An herbal cattle feed supplement composition of claim 2 comprising 30 to 70% (w/w) herbs, 5 to 10% (w/w) probiotics, 5 to 20% (w/w) minerals, 5 to 20% (w/w) protein source, 0 to 1% (w/w) vitamins, 0 to 1% (w/w) amino acids and 5 to 40% (w/w) dicalcium phosphate, dolomite or calcite wherein the combined percentage does not exceed 100%.

4. An herbal cattle feed supplement composition of claim 3 wherein the protein source is decorticated cotton seed extract and/or soya.

5. An herbal cattle feed supplement composition of claim 3 wherein the probiotics comprise a live yeast culture.

6. An herbal cattle feed supplement composition of claim 5 wherein the live yeast culture comprises *Saccharomyces cerevisiae*.

7. An herbal cattle feed supplement composition of claim 3 wherein the minerals are chelated minerals.

8. An herbal cattle feed supplement composition of claim 7 wherein the chelated minerals comprise chelated zinc, chelated manganese, chelated copper; chelated cobalt, chelated selenium, chelated chromium, chelated iodine, chelated methomin and chelated tricalcium phosphate or mixtures thereof.

9. An herbal cattle feed supplement composition of claim 3 wherein the minerals comprise calcium, phosphorous, magnesium, copper, zinc, manganese, iron, cobalt, iodine and sulphur or mixtures thereof.

10. An herbal cattle feed supplement comprising *Asparagus racemosus* or an extract, bioactive fraction or powder therefrom, probiotics and minerals.

11. An herbal cattle feed supplement composition of claim 10 further comprising *Withania somnifera, Lepidium sativum, Bacopa monnieri, Nardostachys jatamamsi, Pueraria tuberosa, Emblica officinalis, Tinospora cordifolia* or extracts, bioactive fractions or powders therefrom.

12. An herbal cattle feed supplement composition of claim 11 further comprising (a) protein source, (b) vitamins (c) amino acids and (d) dicalcium phosphate, dolomite or calcite.

13. An herbal cattle feed supplement composition of claim 12 further comprising *Vetiveria zizanioides* or an extract, bioactive fraction or powder therefrom.

14. An herbal cattle feed supplement composition of claim 12 comprising 30 to 70% (w/w) herbs, 5 to 10% (w/w) probiotics, 5 to 20% (w/w) minerals, 5 to 20% (w/w) protein source, 0 to 1% (w/w) vitamins, 0 to 1% (w/w) amino acids and 5 to 40% (w/w) dicalcium phosphate, dolomite or calcite wherein the combined percentage does not exceed 100%.

15. An herbal cattle feed supplement composition of claim 12 comprising 50% (w/w) herbs, 10% (w/w) probiotics, 15% (w/w) minerals, 10% (w/w) decorticated cotton seed extract, 0.2 to 1% (w/w) vitamins, 0.1 to 1% (w/w) amino acids and 13 to 15% (w/w) dicalcium phosphate, dolomite or calcite wherein the combined percentage does not exceed 100%.

16. An herbal cattle feed supplement composition of claim 15 wherein the probiotics comprise a live yeast culture.

17. An herbal cattle feed supplement composition of claim 16 wherein the live yeast culture comprises *Saccharomyces cerevisiae*.

18. An herbal cattle feed supplement composition of claim 15 wherein the minerals are chelated minerals.

19. An herbal cattle feed supplement composition of claim 18 wherein the chelated minerals comprise chelated zinc, chelated manganese, chelated copper, chelated cobalt, chelated selenium, chelated chromium, chelated iodine, chelated methomin and chelated tricalcium phosphate or mixtures thereof.

20. An herbal cattle feed supplement composition consisting of (i) herbs consisting of *Asparagus racemosus, Withania somnifera, Lepidium sativum, Bacopa monnieri, Nardostachys jatamamsi, Vetiveria zizanioides, Pueraria tuberosa, Emblica officinalis, Tinospora cordifolia* or extracts, bioactive fractions or powders therefrom; and (ii) additives consisting of (a) probiotics, (b) minerals, (c) protein source, (d) vitamins (e) amino acids and (f) dicalcium phosphate, dolomite or calcite.

21. An herbal cattle feed supplement composition of claim 20 wherein the probiotics comprise a live yeast culture comprising *Saccharomyces cerevisiae* and the minerals are chelated minerals.

* * * * *